United States Patent [19]
Ghorashi et al.

[11] Patent Number: 6,020,744
[45] Date of Patent: Feb. 1, 2000

[54] MOISTURE SENSOR

[75] Inventors: Hossein M. Ghorashi; Michael E. Galyon; T. Vaughn Blalock, all of Knoxville, Tenn.

[73] Assignee: Zellweger Uster, Inc., N.C.

[21] Appl. No.: 08/963,855

[22] Filed: Nov. 4, 1997

[51] Int. Cl.[7] .................................................. G01R 27/26
[52] U.S. Cl. ........................... 324/678; 324/664; 324/689
[58] Field of Search .................................... 324/710, 711, 324/712, 677, 678, 689, 679, 664

[56] References Cited

U.S. PATENT DOCUMENTS

| | | |
|---|---|---|
| 2,063,840 | 12/1936 | Fairchild et al. . |
| 3,005,154 | 10/1961 | Moore et al. . |
| 3,370,360 | 2/1968 | Smith . |
| 3,906,471 | 9/1975 | Shawhan .................................. 324/710 |
| 4,266,188 | 5/1981 | Thompson . |
| 4,584,522 | 4/1986 | Varela . |
| 4,639,831 | 1/1987 | Iyoda ...................................... 324/689 |
| 4,816,748 | 3/1989 | Tazawa .................................... 324/711 |
| 4,868,491 | 9/1989 | Black . |
| 5,087,120 | 2/1992 | Anthony . |
| 5,125,279 | 6/1992 | Anthony et al. . |
| 5,218,309 | 6/1993 | Nelson et al. . |
| 5,514,973 | 5/1996 | Byler et al. . |
| 5,656,928 | 8/1997 | Suzuki ..................................... 324/712 |

*Primary Examiner*—Josie Ballato
*Assistant Examiner*—Jose M. Solis
*Attorney, Agent, or Firm*—Luedeka, Neely & Graham, PC

[57] ABSTRACT

An apparatus measures moisture content of cotton based upon rates of electrical charges flowing through the cotton. The apparatus includes a moisture sensor having first electrodes, second electrodes, and ground electrodes which are interdigitated between the first and second electrodes. The apparatus also includes a moisture content determination circuit that provides first electrical charges to the first electrodes, and second electrical charges to the second electrodes. The moisture content determination circuit determines the rate of electrical charge flowing from each of the first and second electrodes through the cotton to the ground electrodes, and determines the moisture content of the cotton based upon the rates of electrical charges flowing through the cotton. By thus applying first electrical charges to the first electrodes and second electrical charges to the second electrodes, the apparatus accurately measures the moisture content of the cotton over a wide range of moisture contents. This wide range is achieved by setting the first electrical charges on the first electrodes to a level which is optimal for moisture levels at the upper end of the desired measurement range, and by setting the second electrical charges on the second electrodes to a level which is optimal for moisture levels at the lower end of the desired measurement range.

29 Claims, 4 Drawing Sheets

MOISTURE SENSOR

TECHNICAL FIELD

This invention relates to the field of measurement of physical properties of flowable materials. More particularly, this invention relates to the field of measurement of the moisture content of cotton being processed in a cotton gin.

BACKGROUND OF THE INVENTION

One factor which determines the quality of cotton fibers produced by a ginning operation is the amount of moisture present in the cotton lint as the lint is cleaned and ginned. Lint cleaning machines operate most efficiently, and do the least amount of damage to the cotton fibers, if the moisture content of the cotton lint is maintained within an optimum range during the cleaning operation. Cotton lint moisture content can be maintained within an optimum range by continuous adjustment of the lint drying equipment based upon the moisture content of the lint exiting the drying equipment.

A typical moisture-measurement system determines moisture content based upon the electrical resistance of the cotton. Such a system captures a sample of the cotton from the cotton flow and compresses the sample between a cathode and an anode. The system then measures the electrical resistance between the cathode and the anode. Since the moisture content of the cotton is inversely proportional to the cotton's electrical resistance, the moisture content may be calculated based upon empirically-determined equations.

Unfortunately, resistance-measurement systems tend to be accurate over a relatively small range of moisture content. As moisture content increases, resistance decreases. As a result, measurement accuracy degrades if the system cannot accurately measure small resistance values. Therefore, as moisture content increases, it is desirable to increase the resistance of the sample such as by increasing the spacing between the cathode and anode. Conversely, as moisture content decreases, the resistance of the cotton increases. This may be compensated for by decreasing the spacing between the cathode and anode which decreases the resistance through the sample. Unfortunately, this solution tends to exacerbate the high-moisture measurement problem.

Due to these disparate design concerns, typical moisture-measurement systems compromise between measurement accuracy at low-moisture levels and high-moisture levels. As a result, the accuracy of these systems is limited to a relatively small range near the center of the range of expected moisture levels. If the moisture-measurement system does not accurately determine moisture content over a sufficiently wide range of moisture levels, then a lint dryer control system tends to maintain less than optimum moisture levels in the cotton. If the lint dryer does not maintain the moisture content within an optimum range during the cleaning operation, the cotton fibers tend to sustain more damage than they would at an optimum moisture level.

What is needed, therefore, is a method and apparatus which accurately measures the moisture content of cotton over a range of moisture levels that is wide enough to provide for optimum control of a cotton lint dryer in a cotton gin.

SUMMARY OF THE INVENTION

The foregoing and other needs are met by an apparatus which measures the moisture content of a material, such as cotton, whose electrical resistance is a function of the material's moisture content. The moisture content measurement is based upon rates of electrical charges flowing through the material. The apparatus has a moisture sensor, containing first electrodes, second electrodes, and ground electrodes. The ground electrodes are interdigitated between the first and second electrodes. The apparatus also includes a moisture content determination circuit that provides first electrical charges to the first electrodes, and second electrical charges to the second electrodes. The moisture content determination circuit determines the rate of electrical charge flowing from each of the first and second electrodes through the material to the ground electrodes, and determines the moisture content of the material based upon the rates of electrical charges flowing through the material.

By thus applying first electrical charges to the first electrodes and second electrical charges to the second electrodes, the present invention accurately measures the moisture content of the material over a wide range of moisture contents. This wide range is achieved by setting the first electrical charges on the first electrodes to a level which is optimal for moisture levels at the upper end of the desired measurement range, and by setting the second electrical charges on the second electrodes to a level which is optimal for moisture levels at the lower end of the desired measurement range. Thus, the typical problems associated with the measurement of moisture content based upon resistance, as described above, are avoided.

In preferred embodiments, the moisture content determination circuit has first electrode charging circuits and second electrode charging circuits. The first electrode charging circuits charge first capacitors to a first voltage level, there being a first capacitor associated with each of the first electrodes. In this manner, the first voltage level is applied to each of the first electrodes. Similarly, the second electrode charging circuits charge second capacitors to the first voltage level, there being a second capacitor associated with each of the second electrodes. The first voltage level is thus also applied to each of the second electrodes.

The moisture content determination circuit also includes a sensor discharge timer for determining first discharge durations that are associated with the first electrodes. The first discharge durations measure the rates at which the first voltage level on the first electrodes decreases to second voltage levels due to the discharge of the first capacitors. The sensor discharge timer also determines second discharge durations that are associated with the second electrodes. The second discharge durations measure the rates at which the first voltage level on the second electrodes decreases to the second voltage level due to the discharge of the second capacitors. The sensor discharge timer includes a clock for producing periodic clock pulses, and a counter for counting the clock pulses while the first voltage level on the first electrodes decreases to the second voltage level as the first capacitors discharge. The counter also counts clock pulses while the first voltage level on the second electrodes decreases to the second voltage level as the second capacitors discharge.

A moisture content calculator of a preferred embodiment determines the moisture content of the material based upon a number of selected first and second discharge durations. The selected first and second discharge durations fall within a selected range of clock pulses. The moisture content calculator determines moisture content using a method which relates the selected first and second discharge durations to the moisture content according to:

$$M = \frac{\sum_{m=1}^{n_1} M_1(m) + \sum_{m=1}^{n_2} M_2(m)}{n_1 + n_2}, \qquad (1)$$

where M is the moisture content of the material expressed as a percentage by weight, wet-basis, $M_1(m)$ is the moisture content of the material determined using an mth selected first discharge duration, where m is an integer between 1 and $n_1$, inclusive, and $M_2(m)$ is the moisture content of the material determined using an mth selected second discharge duration, where m is an integer between 1 and $n_2$, inclusive.

In other preferred embodiments, the first and second electrodes include parallel linear electrical conductors. Each of the first and second electrode conductors are electrically insulated from all other conductors. The ground electrodes include discrete parallel linear electrical conductors which are parallel to and insulated from the first and second electrode conductors. Each of the ground electrodes is at an electrical ground potential.

This invention also provides a method for measuring moisture content of a material based upon rates of electrical charges flowing through the material. First electrical charges are provided to first electrodes, and second electrical charges are provided to second electrodes. The first and second electrical charges are discharged through the material to ground electrodes which are interdigitated between the first and second electrodes. The rates of electrical charges flowing from the first and second electrodes through the material to the ground electrodes are determined. The moisture content of the material is determined based upon the rates of electrical charges flowing from the first electrodes, and based upon the rates of electrical charges flowing from the second electrodes.

In preferred embodiments of the invention, the step of providing first electrical charges to the first electrodes includes the steps of charging first capacitors to a first voltage level and applying the first voltage level to the first electrodes. The step of providing second electrical charges to the second electrodes includes the steps of charging second capacitors to the first voltage level and applying the first voltage level to the second electrodes.

In some preferred embodiments, the step of determining the rates of electrical charges flowing from the first electrodes through the material to the ground electrodes includes the step of determining first discharge durations associated with the first electrodes. The first discharge durations measure the rates at which the first voltage level on the first electrodes decreases to a second voltage level as the first capacitors discharge. Also, the step of determining the rates of electrical charges flowing from the second electrodes through the material to the ground electrodes includes the step of determining second discharge durations associated with the second electrodes. The second discharge durations measure the rates at which the first voltage level on the second electrodes decreases to the second voltage level as the second capacitors discharge.

The first discharge durations of some embodiments are determined by producing periodic clock pulses and counting the clock pulses while the first voltage level on the first electrodes decreases to the second voltage level as the first capacitors discharge. In like manner, the second discharge durations are determined by producing periodic clock pulses and counting the clock pulses while the first voltage level on the second electrodes decreases to the second voltage level as the second capacitors discharge. The moisture content of the material is determined based upon a number of selected first and second discharge durations which fall within a designated range of clock pulses.

In preferred embodiments, the moisture content of the material is determined based upon the selected first and second discharge durations according to:

$$M = \frac{\sum_{m=1}^{n_1} M_1(m) + \sum_{m=1}^{n_2} M_2(m)}{n_1 + n_2}, \qquad (2)$$

where M is the moisture content of the material expressed as a percentage by weight, wet-basis, $M_1(m)$ is the moisture content of the material determined using an mth selected first discharge duration, where m is an integer between 1 and $n_1$, inclusive, and $M_2(m)$ is the moisture content of the material determined using an mth selected second discharge duration, where m is an integer between 1 and $n_2$, inclusive.

This invention further provides a method for measuring moisture content of cotton based upon rates of electrical charges flowing through the cotton. First electrical charges are provided to first electrodes by charging a set of first capacitors to a first voltage level and applying the first voltage level to the first electrodes. Each of the first capacitors has a capacitance of about one microfarad. Second electrical charges are provided on second electrodes by charging a set of second capacitors to the first voltage level and applying the first voltage level to the second electrodes. Each of the second capacitors has a capacitance of about 270 picofarads. The first and second electrical charges are discharged through the cotton to ground electrodes which are interdigitated between the first and second electrodes.

First discharge durations and second discharge durations are determined. The first discharge durations measure the rates at which the first voltage level on the first electrodes decreases to a second voltage level due as the first capacitors discharge. Similarly, the second discharge durations measure the rates at which the first voltage level on the second electrodes decreases to the second voltage level as the second capacitors discharge. The first discharge durations are determined by producing periodic clock pulses at a rate of about two megahertz and counting the clock pulses while the first voltage level on the first electrodes decreases to the second voltage level. In like manner, the second discharge durations are determined by producing periodic clock pulses at a rate of about two megahertz and counting the clock pulses while the first voltage level on the second electrodes decreases to the second voltage level. The moisture content of the cotton is determined based upon a number of selected first and second discharge durations falling within a selected range of about 2000 to about $10^7$ clock pulses. This range of selected range of clock pulses is equivalent to a time period of about one millisecond to about five seconds. The moisture content is determined according to:

$$M = \frac{\sum_{m=1}^{n_1} M_1(m) + \sum_{m=1}^{n_2} M_2(m)}{n_1 + n_2}, \qquad (3)$$

where M is the moisture content of the cotton expressed as a percentage by weight, wet-basis, $$M_1(m) = \ln\left[\left(\frac{1.171 \times 10^{13}}{N_1(m)}\right)^{0.663}\right], \quad (4)$$

and $$M_2(m) = \ln\left[\left(\frac{3.396 \times 10^9}{N_2(m)}\right)^{0.663}\right]. \quad (5)$$

In the above equations, $n_1$ is the number of selected first discharge durations that are in the selected range, and $n_2$ is the number of selected second discharge durations that are in the selected range. $M_1(m)$ is the moisture content of the cotton determined using an mth selected first discharge duration, where m is an integer between 1 and $n_1$, inclusive. $M_2(m)$ is the moisture content of the cotton determined using the mth selected second discharge duration, where m is an integer between 1 and $n_2$, inclusive. $N_1(m)$ is the mth selected first discharge duration in clock pulses, and $N_2(m)$ is the mth selected second discharge duration in clock pulses.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows.

DETAILED DESCRIPTION OF THE INVENTION

The present invention is used to measure the moisture content of cotton, such as cotton being processed in a ginning operation. Although the detailed description of the invention is directed toward moisture measurement of cotton fiber, it will be appreciated that the invention may also be used to measure the moisture content of other materials having mass flow properties, which can be compressed against a planar surface, and which has electrical conductivity dependant on moisture content and within a measurable range.

Figure 1:
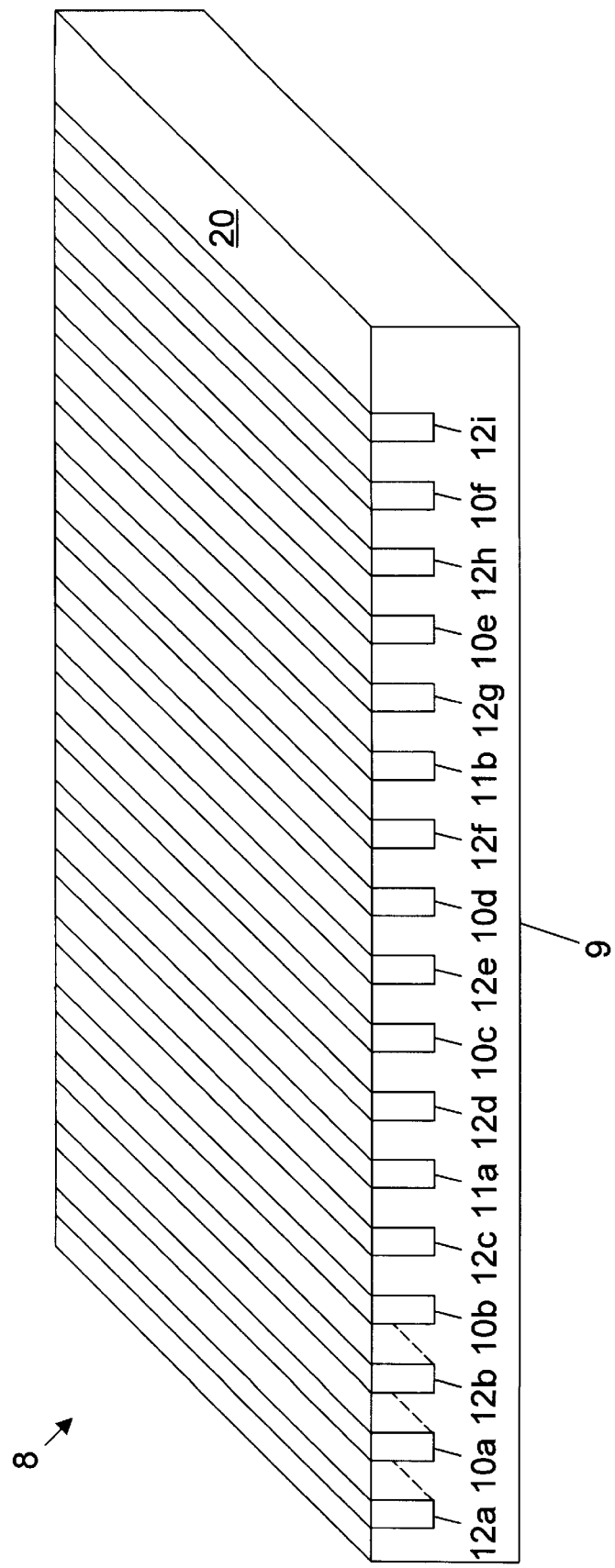
FIG. 1 is a perspective view of a moisture sensor probe.

Referring now to FIG. 1, a preferred embodiment of a moisture sensor (indicated generally at 8) is depicted. The moisture sensor 8 includes a measurement block 9 having a planar measurement surface 20. The measurement block 9 is formed from electrically-nonconductive, high-resistance material having low moisture absorption properties, such as Teflon. Preferably, the measurement block 9 is formed from material which maintains its nonconductive characteristics upon prolonged exposure to moisture. Within the measurement block 9, there is an array of sensor electrodes consisting of first electrodes 11a–11b and second electrodes 10a–10f. The first electrodes 11a–11b and second electrodes 10a–10f are parallel linear electrical conductors formed from a highly-conductive metal, such as copper, aluminum, or stainless steel. The first electrodes 11a–11b and the second electrodes 10a–10f are embedded in the measurement block 9 with their edges exposed through the measurement surface 20.

Also embedded in the measurement block 9 is an array of ground electrodes 12a–12i, which are discrete parallel linear electrical conductors interdigitated within the array of first electrodes 11a–11b and second electrodes 10a–10f. As indicated in FIG. 1, each of the first electrodes and second electrodes is flanked on either side by two of the ground electrodes 12a–12i. The ground electrodes 12a–12i, which are all electrically grounded, are also formed from a highly-conductive metal. The ground electrodes also have edges which are exposed through the measurement surface 20.

Although the following description discloses a moisture-sensing device having two first electrodes 11a–11b, six second electrodes 10a–10f, and nine ground electrodes 12a–12i, it will be appreciated that the invention is not limited by any particular number of electrodes. One limitation on the number of ground electrodes is that their number is preferably at least one greater than the sum of the first and second electrodes.

In one typical application, the measurement block 9 may be incorporated into the inner wall of a duct, pipe, or similar conduit through which cotton is flowing. Although the measurement surface 20 depicted in FIG. 1 is planar, the measurement surface 20 could also be curved, such as a section of a cylindrical or conical surface. The shape of the measurement surface 20 is not of prime significance as long as the material whose moisture content is being measured sufficiently contacts the measurement surface 20.

Figure 2:
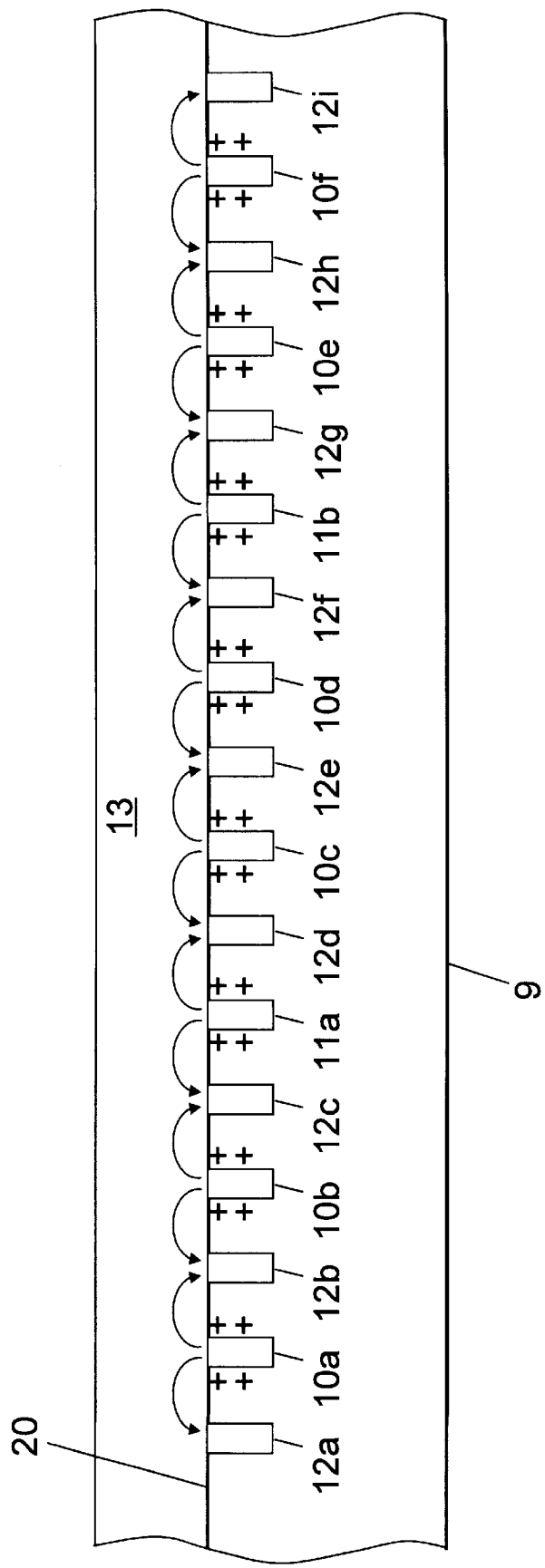
FIG. 2 is an edge view of the moisture sensor probe.

Shown in FIG. 2 is an edge view of a preferred embodiment of the measurement block 9 with a sample of cotton 13 adjacent to the measurement surface 20. The cotton 13 preferably makes continuous contact with the first electrodes 11a–11b, the second electrodes 10a–10f, and the ground electrodes 12a–12i. If a positive electrical charge is placed upon the first electrodes 11a–11b (as indicated by the "+" symbols), then an electrical potential exists between the first electrodes 11a–11b and the ground electrodes 12a–12i. Similarly, if a positive electrical charge is placed upon the second electrodes 10a–10f, then an electrical potential exists between the second electrodes 10a–10f and the ground electrodes 12a–12i.

If the cotton 13 is completely dry, it tends to be essentially electrically nonconductive, and no appreciable charge flows from the first electrodes 11a–11b or the second electrodes 10a–10f to the ground electrodes 12a–12i. However, as the moisture content of the cotton 13 increases, so does its conductivity. Therefore, as the moisture content of the cotton 13 increases, the rate of charge flowing from the first electrodes 11a–11b and second electrodes 10a–10f to the ground electrodes 12a–12i also increases. As indicated in FIG. 2, the charge tends to flow (as indicated by the arrows) from a positively charged electrode, such as the first electrode 11a, to the nearest two ground electrodes, such as the ground electrodes 12c and 12d. If the charge on the first electrodes 11a–11b and the second electrodes 10a–10f is not replenished as the charge flows to the ground electrodes 12a–12i, then the electrical potential on the first electrodes 11a–11b and second electrodes 10a–10f gradually decreases relative to the potential on the ground electrodes 12a–12i.

If the time required for the electrical potential on the first electrodes 11a–11b to drop from an initial value to a lower value is known, then the rate of charge flowing from the first electrodes 11a–11b to the ground electrodes 12a–12i can be determined. Similarly, if the time required for the electrical potential on the second electrodes $10a$–$10f$ to drop from an initial value to a lower value is known, then the rate of charge flowing from the second electrodes $10a$–$10f$ to the ground electrodes $12a$–$12i$ can be determined. The moisture content of the cotton 13 can then be determined based upon the rate of charge flowing through the cotton 13.

Figure 3:
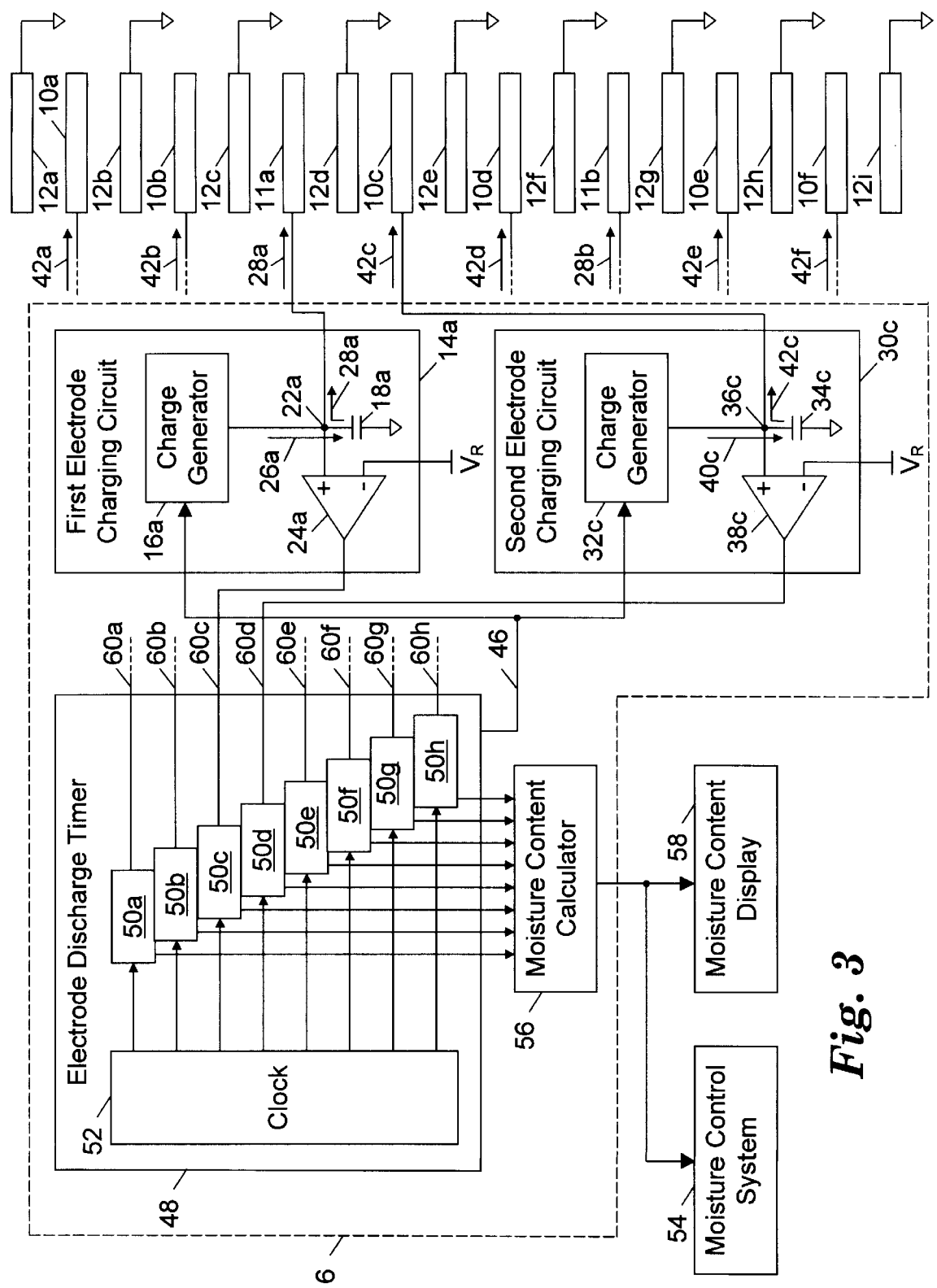
FIG. 3 is a functional block diagram of the moisture sensor.

Shown in FIG. 3 is a functional block diagram of a moisture content determination circuit 6 according to a preferred embodiment of the present invention. The first electrodes $11a$–$11b$ and the second electrodes $10a$–$10f$ are also shown interdigitated with the array of ground electrodes $12a$–$12i$. In the preferred embodiment, the first electrodes $11a$–$11b$ are physically identical to the second electrodes $10a$–$10f$. However, the first electrodes $11a$–$11b$ are connected to first electrode charging circuits, and the second electrodes $10a$–$10f$ are connected to second electrode charging circuits. In the interest of clarity, FIG. 3 depicts only one first electrode charging circuit $14a$, which is connected to the first electrode $11a$, and only one second electrode charging circuit $30c$, which is connected to the second electrode $10c$. It will be appreciated that the other first electrode $11b$ is connected to a first electrode charging circuit that is not depicted in FIG. 3 so as not to unnecessarily encumber the drawing, but which is identical to the first electrode charging circuit $14a$. It will also be appreciated that the other second electrodes $10a$, $10b$, $10d$, $10e$, and $10f$ are connected to other second electrode charging circuits which are also not depicted in FIG. 3, but which are also preferably identical to the second electrode charging circuit $30c$.

With continued reference to FIG. 3, a moisture measurement is initiated by an electrode discharge timer 48 which sends a start-charge signal over the line 46 to a first electrode charging circuit $14a$. The first electrode charging circuit $14a$ includes a charge generator $16a$ which is connected to the first electrode $11a$ and a first capacitor $18a$ at a node $22a$. The other side of the first capacitor $18a$ is grounded. When the charge generator $16a$ receives the start-charge signal, the charge generator $16a$ generates a first electrical charge which is stored in the first capacitor $18a$. The flow of charge from the charge generator $16a$ to the first capacitor $18a$ is indicated in FIG. 3 by a charging current $26a$. When the charge generator $16a$ receives a stop-charge signal over the line 46 from the electrode discharge timer 48, the charge generator $16a$ stops generating charge, and the first electrical charge which is stored in the first capacitor $18a$ begins to discharge.

As shown in FIG. 3, there are three possible paths for the charge on the first capacitor $18a$ to take: back to the charge generator $16a$, to a voltage comparator $24a$, or to the first electrode $11a$. Since the input impedances to the voltage comparator $24a$ and the charge generator $16a$ are preferably very high relative to the third option, the only available discharge path to ground is via the first electrode $11a$. This flow of charge from the first capacitor $18a$ to the first electrode $11a$ is indicated in FIG. 3 by a discharge current $28a$. Thus, the charge on the first capacitor $18a$ tends to flow from the first electrode $11a$ through the cotton 13 to the nearest ground electrodes $12c$ and $12d$. This discharge flow continues until the charge on the first capacitor $18a$ is depleted, or until the current $28a$ is otherwise interrupted.

As the discharge current $28a$ flows from the node $22a$, the voltage on the node $22a$ decreases from a first voltage level which existed at the instant that the discharge signal was sent by the electrode discharge timer 48. The voltage on the node $22a$ is compared to a reference voltage $V_R$ in the comparator $24a$. The electrode discharge timer 48 includes a counter $50c$ which senses the initial logic voltage level on the line $60c$.

The sensor discharge timer 48 also includes a clock 52 which creates periodic clock pulses at a rate of about two MHZ in the preferred embodiment. It will be appreciated that other clock rates could be implemented depending upon the allotted measurement time. Preferably, the electrode discharge timer 48, including the clock 52 and the counter $50c$, is implemented in a microprocessor-based computer.

When the stop-charge signal is sent to the charge generator $16a$, the counter $50c$ begins counting clock pulses while sensing the voltage level on the line $60c$. In a preferred embodiment, the first voltage level on the line $60c$ is a logic-high level, such as five volts. As the first capacitor $18a$ discharges, the voltage level at the positive input of the comparator $24a$ decreases. When the voltage level at the positive input of the comparator $24a$ drops to a level approaching the reference voltage $V_R$, the voltage at the output of the comparator $24a$ drops to a logic-low level. When the voltage level at the output of the comparator $24a$, which is the voltage on the line $60c$, drops to the logic-low level, the counter $50c$ stops counting. Thus, a first discharge duration associated with the first electrode $11a$ is determined by the number of clock pulses which the counter $50c$ counts as the voltage at the positive input to the comparator $24a$ drops from the first, or initial value to the second, or subsequent value.

Also shown in FIG. 3 is a second electrode charging circuit $30c$ which includes a charge generator $32c$ and a second capacitor $34c$ that are connected to one of the second electrodes $10c$ at the node $36c$. The positive input to the voltage comparator $38c$ is also connected to the node $36c$, and the output of the comparator $38c$ is connected to the line $60d$. The operation of the second electrode charging circuit $30c$ is similar to the operation of the first electrode charging circuit $14a$ as described above. However, one of the significant differences between the two sensor charging circuits is the difference in size of the capacitors $18a$ and $34c$. Due to this difference in capacitance, the second electrical charge which forms on the second capacitor $34c$ is smaller than the first electrical charge which forms on the first capacitor $18a$. This difference in charge levels, and its impact on the operation of the invention, is discussed in greater detail hereinafter.

With continued reference to FIG. 3, the counters $50c$ and $50f$ sense the voltage levels on the lines $60c$ and $60f$, respectively, as the first electrode discharge currents $28a$ and $28b$ are flowing, and determines pulse count values representing the first discharge durations associated with the first electrodes $11a$ and $11b$. The counters $50a$, $50b$, $50d$, $50e$, $50g$, and $50h$ sense the voltage levels on the lines $60a$, $60b$, $60d$, $60e$, $60g$ and $60h$, respectively, as the second electrode discharge currents $42a$–$42f$ are flowing, and determines pulse count values representing the second discharge durations associated with the second electrodes $10a$–$10f$. These eight pulse count values are passed to a moisture content calculator 56.

The moisture content calculator 56, such as a microprocessor-based computer, determines the moisture content of the cotton 13 based upon the eight pulse count values from the counters $50a$–$50h$. The moisture content calculator 56 first discards any of the pulse count values which fall outside a designated range of clock pulses. In a preferred embodiment, the designated range is 2000 to $10^7$ pulses. When using the preferred two MHZ clock, this range is equivalent to a time window of about one millisecond to about five seconds. Thus, only selected discharge durations, that is, those with pulse counts of no less than about 2000 and no greater than about $10^7$, are used in the moisture content determination according to the preferred embodiment. Using the selected discharge durations, the moisture content calculator determines the moisture content of the cotton 13 according to:

$$M = \frac{\sum_{m=1}^{n_1} M_1(m) + \sum_{m=1}^{n_2} M_2(m)}{n_1 + n_2}, \quad (6)$$

where M is the moisture content expressed as a wet basis percentage. $M_1(m)$ in the above expression is the cotton moisture content percentage determined using the mth selected first discharge duration out of a total of $n_1$ selected first discharge durations from the first electrodes 11a and 11b. $M_2(m)$ is the cotton moisture content percentage determined using the mth selected second discharge duration out of a total of $n_2$ selected second discharge durations from the second electrodes 10a–10f. $M_1(m)$ is determined according to:

$$M_1(m) = \ln\left[\left(\frac{1.171 \times 10^{13}}{N_1(m)}\right)^{0.663}\right], \quad (7)$$

where $N_1(m)$ is the mth selected first discharge duration, expressed in clock 52 pulses, from a first electrode. $M_2(m)$ is determined according to:

$$M_2(m) = \ln\left[\left(\frac{3.396 \times 10^9}{N_2(m)}\right)^{0.663}\right], \quad (8)$$

where $N_2(m)$ is the mth selected second discharge duration, expressed in clock 52 pulses, from a second electrode. The coefficients in the equations given above have been determined for an initial voltage value of about 6.9 volts and a lower voltage value of about 4.64 volts. The coefficients for other voltage values could also be determined.

In a preferred embodiment of the invention, $n_1$ is 2 and $n_2$ is 6. However, it should be apparent that the method of determining moisture content according to the present invention is not limited to any particular value of $n_1$ or $n_2$. Further, the invention is not limited to any specific relationship between the values of $n_1$ and $n_2$.

In a typical application of the invention, the moisture content calculator 56 passes the moisture content value, M, to a moisture control system 54 within the ginning operation. The moisture control system 54 is a device, such as a cotton lint dryer, which uses the moisture content value to adjust the moisture content of the cotton for the least cotton fiber damage and the most efficient ginning operation. The moisture content value is also passed to a moisture content display 58, such as a digital numerical display, which may be observed by an operator.

As mentioned previously, one difference between the first electrode charging circuit 14a and the second electrode charging circuit 30c is the difference in size of the capacitors 18a and 34c. In a preferred embodiment, the first electrode charging circuit 14a incorporates a one microfarad capacitor 18a, whereas the second electrode charging circuit 30c incorporates a 270 picofarads capacitor 34c. The first capacitor 18a has approximately 3700 times the charge-storage capacity of the second capacitor 34c. Thus, when the two capacitors 18a and 34c are charged to the same initial voltage level, the first capacitor 18a takes a longer time to discharge than the second capacitor 34c. This is true if the two discharge currents 28a and 42c are flowing through paths having the same conductance, such as through the same sample of cotton 13.

By incorporating capacitors 18a and 34c which have different discharge durations for the same cotton moisture content, the range of moisture content that can be measured during an optimum discharge duration time is increased. For example, if the sample of cotton 13 has a moisture content of 14.9 percent, then the potential across the one microfarad capacitor 18a drops from 6.9 volts to 4 volts in about one millisecond. One millisecond is equivalent to 2000 pulses of the two MHZ clock 52, a value which is within the optimum discharge duration range.

However, if the sample of cotton 13 has a moisture content of only 3.9 percent, then the one microfarad capacitor 18a would typically require over $3 \times 10^{10}$ pulses of the two MHZ clock 52 (over four hours) to discharge from a potential of 6.9 volts down to 4.64 volts. Such a long discharge time is inconsistent with the need for a quick moisture measurement, and thus falls well outside the preferred discharge duration range.

On the other hand, a 6.9 volt initial potential on the 270 picofarads capacitor 34c drops to 4.64 volts in about $9.48 \times 10^6$ pulses (about five seconds) when discharging through the cotton 13 having a 3.9 percent moisture content. Since the typical moisture-control system in a ginning operation requires many moisture measurement updates per minute, a discharge time of less than five seconds, as provided by the 270 picofarads capacitor 34c, is preferred for low-moisture measurements. However, 270 picofarads is not an optimal size for measuring cotton which has high moisture content. For instance, it takes less than one pulse of the two MHZ clock 52 to discharge the second capacitor 34c through cotton 13 with 14.9 percent moisture content. Such a discharge duration tends to be too short to be resolved with the clock 52 of the preferred embodiment.

The previous examples illustrate the complementary nature of the dual-range moisture sensor approach of the present invention. By incorporating second electrode charging circuits capable of measuring moisture from about 3.9 percent to about 9.5 percent, and first electrode charging circuits capable of measuring moisture from about 9.3 percent to about 14.9 percent, the preferred embodiment of the invention accurately measures moisture content over an 11 percent wide range. Thus, the moisture measurement range of the present invention is more than about twice as large as the range covered by prior devices.

Based upon this discussion, it will be recognized that the moisture sensing range of the invention could be further extended by including other sets of electrodes that are charged by capacitors that are larger or smaller than those of the preferred embodiment. For example, a set of third electrodes could be charged by third electrode charging circuits incorporating capacitors larger than one microfarad. The charge level on such third electrodes could extend the moisture measurement range to moisture levels of even greater than 14.9 percent. Similarly, a set of fourth electrodes could be charged by fourth electrode charging circuits incorporating capacitors smaller than 270 picofarads. The level of charge on these fourth electrodes could extend the moisture measurement range to moisture levels of even less than 3.9 percent. At some point the size of the capacitors may be reduced to the point where the leakage current is more of an appreciable factor. However, circuits having less leakage current than those described herein could then be used. Therefore, it will be appreciated that the scope of the invention is not limited to only two electrode charging levels.

It will also be recognized that the different levels of charge which are applied to the first and second electrodes of the preferred embodiment could be achieved by means other than different size capacitors. The different levels of charge could be achieved by applying different initial voltage levels to the first and second electrodes prior to discharge. For example, in an alternative embodiment, a third voltage level is applied to the first electrodes, and a fourth voltage level is applied to the second electrodes, where the third voltage level is higher than the fourth voltage level. The higher initial voltage level on the first electrodes results in a higher level of charge on the first electrodes than is on the second electrodes. In this alternative embodiment, the first discharge durations are determined by measuring the time required for the third voltage level on the first electrodes to decrease to a fifth voltage level as the discharge current flows from the first electrodes to the ground electrodes. Similarly, the second discharge durations are determined by measuring the time required for the fourth voltage level on the second electrodes to decrease to a sixth voltage level as the discharge current flows from the second electrodes to the ground electrodes. The fifth and sixth voltage levels of this alternative embodiment could be the same or different voltage levels.

Figure 4:
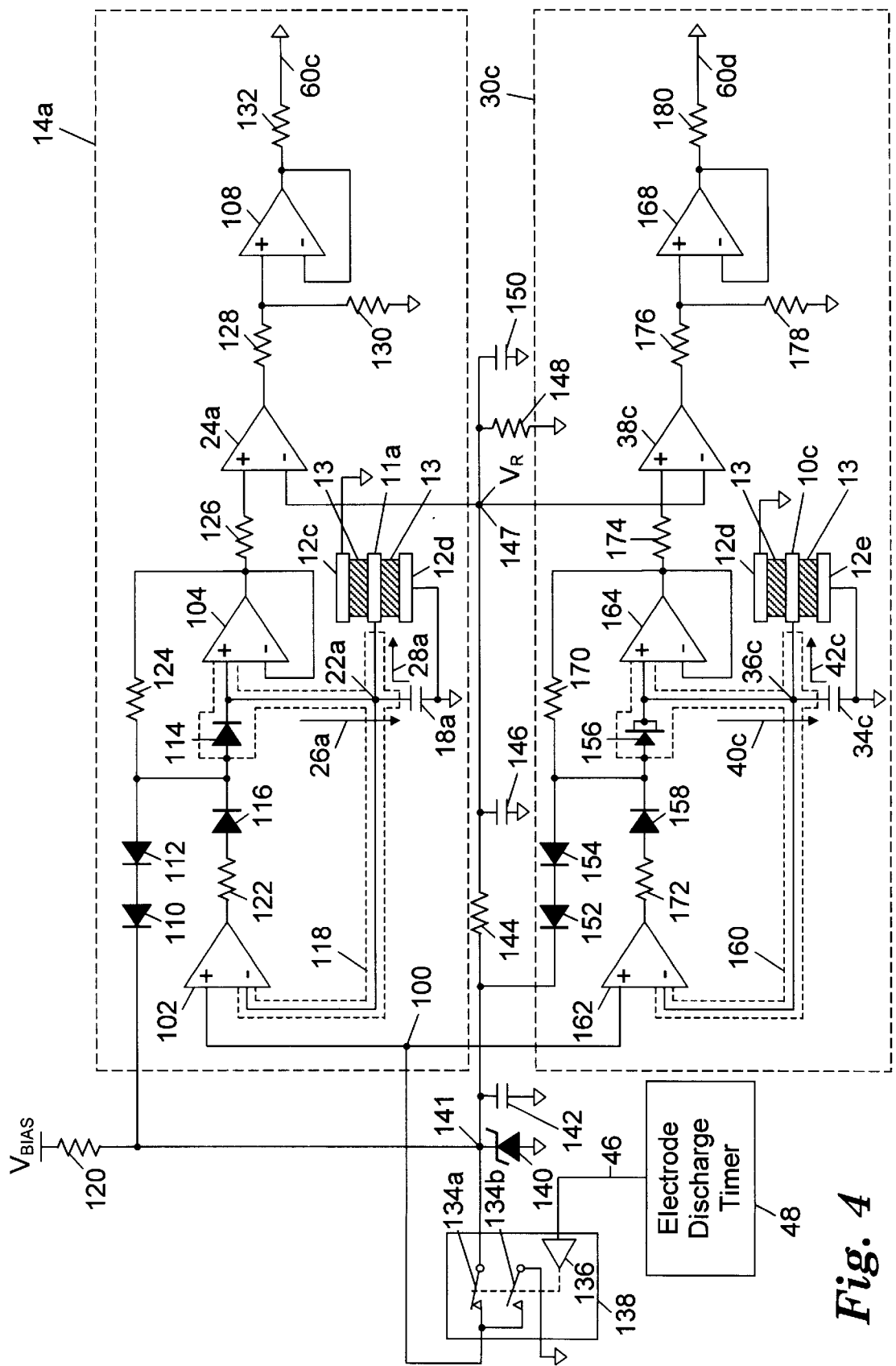
FIG. 4 is a schematic diagram of a first electrode charging circuit and a second electrode charging circuit.

With reference now to FIG. 4, a more detailed description of a preferred embodiment of the first electrode charging circuit 14a will be given. It will be appreciated that the following description applies as well to the first electrode charging circuit 14b which is equivalent in function to the charging circuit 14a. To begin the charging portion of a moisture measurement, the electrode discharge timer 48 sets the voltage on the line 46 to a logic-high level. The line 46 is connected to a solid state switching device 138, such as a device manufactured by Analog Devices having part number ADG419, which responds to the logic-high level by driving the solid-state switches 134a and 134b to the positions shown in FIG. 4: the switch 134a closed and the switch 134b open. In this condition, the voltage at the node 100, which is at the positive 10 input to the operational amplifier (opamp) 102, assumes the same voltage level as at the node 141 at the forward end of the Zener diode 140. The output of the opamp 102 is connected through the resistor 122 and the diodes 116 and 114 to the node 22a. Also connected to the node 22a is the negative input to the opamp 102, the first capacitor 18a, and the first electrode 11a. The opamp 102, acting as a differential-input amplifier, charges the first capacitor 18a until the voltage at the node 22a is nearly equivalent to the voltage at the node 100.

The voltage at the node 22a, which is the voltage across the first capacitor 18a and across the cotton sample 13, is also present at the positive input to the opamp 104. The opamp 104 is a unity gain buffer with a very high impedance input connected to the node 22a. The output of the opamp 104 drives the comparator 24a, a guard ring 118 (indicated in FIG. 4 as a dashed line), and the anodes of the diodes 112 and 114. The guard ring 118 minimizes the surface leakage current on the printed circuit board. The connection of the output of the opamp 104 through the resistor 124 to the anode of the diode 114 causes near zero voltage to appear across the diode 114 during the discharge of the capacitor 18a, thus minimizing leakage current through the diode 114. The reference voltage $V_R$ (typically about 4.7 volts) at the node 147 is applied to the negative input of the comparator 24a. At the time that the capacitor 18a has discharged down to the second voltage, the output of comparator 24a drops to the logic-low level from the logic-high level held during discharge of the capacitor 18a. The resistors 128 and 130 attenuate the output logic levels of the comparator 24a to levels appropriate for transmission through the buffer opamp 108. The output of the buffer 108 appears on the line 60c. As shown in FIG. 3, the line 60c is connected to an input of the counter 50c of the electrode discharge timer 48. In a preferred embodiment of the invention, the initial voltage level on the line 60c is a logic-high level.

The electrode discharge timer 48 waits about 100 milliseconds from the time that it set the high-logic voltage on the line 46, during which time the first capacitor 18a charges, and then sets the voltage on the line 46 to a logic-low level. As a result, the switching device 138 changes state, thus opening the switch 134a and closing the switch 134b. In this condition, the positive input to the opamp 102 is grounded, and the voltage level at the output of the opamp 102 drops. The charge on the first capacitor 18a, seeking the lowest-impedance path to ground, creates a discharge current 28a flowing to the first electrode 11a, through the cotton 13, and to the ground electrodes 12c and 12d. A relatively insignificant amount of the charge flows to the negative input of the opamp 102, the positive input of the opamp 104, and the reverse-biased diode 114, all of which present relatively very high impedances.

At about the same instant that the electrode discharge timer 48 sets the voltage on the line 46 to a logic-low level, the counter 50c resets to zero and begins counting clock pulses. The counter 50c continues to count until the voltage on the line 60c drops to the logic-low level. The moisture content calculator 56 then reads the value of the counter 50c into the variable $N_1(1)$.

Although in the interest of clarity, FIG. 4 shows the schematic diagram of a single first electrode charging circuit 14a, the preferred embodiment of the invention incorporates another first electrode charging circuit 14b which is connected to the first electrode 11b. The first electrode charging circuit 14b is most preferably identical to the first electrode charging circuit 14a, and both circuits may share the common nodes 100, 141, and 147. As a result, the charging and discharging portions of a measurement sequence, as described above for the first electrode charging circuit 14a, occur in the same manner with the first electrode charging circuit 14b. At the completion of the discharging portion of the measurement sequence, the moisture content calculator 56 reads the value of the counter 50d, which is associated with the first electrode charging circuit 14b, into the variable $N_1(2)$.

With continued reference to FIG. 4, a more detailed description of a preferred embodiment of the second electrode charging circuit 30c will be given. It will be appreciated that the following description applies as well to the second electrode charging circuits 30a, 30b, and 30d–30f which are preferably equivalent in function to the charging circuit 30c. To begin the charging portion of a moisture measurement, the electrode discharge timer 48 sets the voltage on the line 46 to a logic-high level. The line 46 is connected to the solid state switching device 138 which responds to the logic-high level by driving the solid-state switches 134a and 134b to the positions shown in FIG. 4: switch 134a closed and switch 134b open. In this condition, the voltage at the node 100, which is at the positive input to the opamp 162, assumes the same voltage level as at node 141 at the forward end of the Zener diode 140. The output of the opamp 162 is connected through the resistor 172, the diode 158, and the JFET 156 to the node 36c. Also connected to the node 36c is the negative input to the opamp 162, second capacitor 34c, and the second electrode 10c. The opamp 162, acting as a differential-input amplifier, charges the second capacitor 34c until the voltage at the node 36c is nearly equivalent to the voltage at the node 100.

The voltage at the node 36c, which is the voltage across the second capacitor 34c and across the cotton sample 13, is also present at the positive input to the opamp 164. The opamp 164 is a unity gain buffer with a very high impedance input connected to the node 36c. The output of the opamp 164 drives the comparator 38c, a guard ring 160 (indicated in FIG. 4 as a dashed line), the anodes of the diodes 154 and 158, and the gate of JFET 156, connected as a diode. The guard ring 160 minimizes the surface leakage current on the printed circuit board. The connection of the output of the opamp 164 through the resistor 170 to the gate of the JFET 156 causes near zero voltage to appear across the JFET 156 during the discharge of the capacitor 34c, thus minimizing leakage current through the JFET 156.

The reference voltage $V_R$ (typically about 4.7 volts) at the node 147 is applied to the negative input of the comparator 38c. At the time that the capacitor 34c has discharged down to the second voltage, the output of comparator 38c drops to the logic-low level from the logic-high level held during discharge of the capacitor 34c. The resistors 176 and 178 attenuate the output logic levels of the comparator 38c to levels appropriate for transmission through the buffer opamp 168. The output of the buffer 168 appears on the line 60d. As shown in FIG. 3, the line 60d is connected to the counter 50d of the electrode discharge timer 48. In a preferred embodiment of the invention, the initial voltage level on the line 60d is a logic-high level.

The electrode discharge timer 48 waits about 100 milliseconds from the time that it set the high-logic voltage on the line 46, during which time the second capacitor 34c charges, and then sets the voltage on the line 46 to a logic-low level. As a result, the switching device 138 changes state, thus opening the switch 134a and closing the switch 134b. In this condition, the positive input to the opamp 162 is grounded, and the voltage level at the output of the opamp 162 drops. The charge on the second capacitor 34c, seeking the lowest-impedance path to ground, creates a discharge current 42c flowing to the second electrode 10c, through the cotton 13, and to the ground electrodes 12d and 12e. A relatively insignificant amount of the charge flows to the negative input of the opamp 162, the positive input of the opamp 164, and into the gate/channel of the JFET 156 connected as a diode, all of which present relatively very high impedances.

When the electrode discharge timer 48 sets the voltage on the line 46 to a logic-low level, the counter 50d resets to zero and begins counting clock pulses, and continues counting until the voltage on the line 60d drops to the logic-low level. The moisture content calculator 56 then reads the value of the counter 50d into the variable $N_2(3)$.

Although in the interest of clarity, FIG. 4 shows the schematic diagram of only one second electrode charging circuit 30c, the preferred embodiment of the invention incorporates five other second electrode charging circuits 30a, 30b, 30d, 30e, and 30f, which are connected to the second electrodes 10a, 10b, 10d, 10e, and 10f. The second electrode charging circuits 30a, 30b, 30d, 30e, and 30f are preferably identical to the second electrode charging circuit 30c, and all of the circuits may share the common nodes 100, 141, and 147. As a result, the charging and discharging portions of a measurement sequence, as described above for the second electrode charging circuit 30c, occur in the same manner with the second electrode charging circuits 30a, 30b, 30d, 30e, and 30f. At the completion of the discharging portion of the measurement sequence, the moisture content calculator 56 reads the values of the counters 50a, 50b, 50e, 50g, and 50h into the variables $N_2(1)$, $N_2(2)$, $N_2(4)$, $N_2(5)$, and $N_2(6)$ for the second electrode charging circuits 30a, 30b, 30d, 30e, and 30f, respectively.

Although in the preferred embodiment of the invention, the first and second electrical charges are applied at the same time to separate sets of sensor electrodes, it will be appreciated that the first and second electrical charges could also be applied to the same set of sensor electrodes at different times. For example, the sensor electrodes could be connected to switches which connect the sensor electrodes to first charging circuits or second charging circuits depending on the state of the switch. In this alternative embodiment, the measurement sequence begins with each of the sensor electrodes connected to corresponding first charging circuits. After the first electrical charges are discharged through the material and the first discharge durations have been determined, the switches change state, thus connecting the sensor electrodes to the second charging circuits. The second charging circuits then apply the second electrical charges to the sensor electrodes, the second electrical charges are discharged through the material, and the second discharge durations are determined. From this point, the determination of the moisture content based on the first and second discharge durations proceeds in the same manner as discussed previously for the preferred embodiment. It will be appreciated that this measurement sequence could be reversed, with the second discharge durations determined before the first discharge durations.

It is contemplated, and will be apparent to those skilled in the art from the preceding description and the accompanying drawings, that modifications and changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. An apparatus for measuring moisture content of a material based upon rates of electrical charges flowing through the material, the apparatus comprising:
   a moisture sensor having:
   first electrodes,
   second electrodes, and
   ground electrodes interdigitated between the first electrodes and the second electrodes; and
   a moisture content determination circuit for providing a first electrical charge to the first electrodes and providing a second electrical charge to the second electrodes, where the first electrical charge and the second electrical charge are at different levels of charge, for measuring the rates of the electrical charges flowing from each of the first and second electrodes through the material to the ground electrodes, and for determining the moisture content of the material based upon the rates of the electrical charges flowing through the material.

2. The apparatus of claim 1 wherein the moisture content determination circuit further comprises:
   electrode charging circuits including:
   first electrode charging circuits, each having a first capacitor associated with one of the first electrodes, the first capacitor charged to a first voltage level, the first voltage level applied to the associated one of the first electrodes, and
   second electrode charging circuits, each having a second capacitor associated with one of the second electrodes, the second capacitor charged to the first voltage level, the first voltage level applied to the associated one of the second electrodes;

a discharge timer for determining first discharge durations associated with the first electrodes and for determining second discharge durations associated with the second electrodes, the first discharge durations measuring the rates at which the first voltage level on the first electrodes decreases to a second voltage level as the first capacitors discharge, the second discharge durations measuring the rates at which the first voltage level on the second electrodes decreases to the second voltage level as the second capacitors discharge; and a moisture content calculator for determining the moisture content of the material based upon the first and second discharge durations.

3. The apparatus of claim 2 wherein the discharge timer further comprises:

a clock for producing periodic clock pulses; and at least one counter for counting the clock pulses while the first voltage level on the first electrodes decreases to the second voltage level as the first capacitors discharge, and for counting the clock pulses while the first voltage level on the second electrodes decreases to the second voltage level as the second capacitors discharge.

4. The apparatus of claim 3 wherein the moisture content calculator determines the moisture content of the material based only upon a number of selected first discharge durations and a number of selected second discharge durations, the selected first discharge durations and selected second discharge durations falling within a designated range of clock pulses.

5. An apparatus for measuring moisture content of a material based upon rates of electrical charges flowing through the material, the apparatus comprising:

a moisture sensor having:
 first electrodes
 second electrodes, and
 ground electrodes interdigitated between the first electrodes and the second electrodes;

a moisture content determination circuit for providing a first electrical charge to the first electrodes and providing a second electrical charge to the second electrodes, where the first electrical charge and the second electrical charge are at different levels of charge, for measuring the rates of the electrical charges flowing from each of the first and second electrodes through the material to the ground electrodes, and for determining the moisture content of the material based upon the rates of the electrical charges flowing through the material, the moisture content determination circuit including:

electrode charging circuits including:
 first electrode charging circuits, each having a first capacitor associated with one of the first electrodes, the first capacitor charged to a first voltage level, the first voltage level applied to the associated one of the first electrodes, and
 second electrode charging circuits, each having a second capacitor associated with one of the second electrodes, the second capacitor charged to the first voltage level, the first voltage level applied to the associated one of the second electrodes;

a discharge timer for determining first discharge durations associated with the first electrodes and for determining second discharge durations associated with the second electrodes, the first discharge durations measuring the rates at which the first voltage level on the first electrodes decreases to a second voltage level as the first capacitors discharge, the second discharge durations measuring the rates at which the first voltage level on the second electrodes decreases to the second voltage level as the second capacitors discharge, the discharge timer including:

a clock for producing periodic clock pulses, and at least one counter for counting the clock pulses while the first voltage level on the first electrodes decreases to the second voltage level as the first capacitors discharge, and for counting the clock pulses while the first voltage level on the second electrodes decreases to the second voltage level as the second capacitors discharge; and, a moisture content calculator for determining the moisture content of the material based only upon a number of selected first discharge durations and a number of selected second discharge durations, the selected first discharge durations and selected second discharge durations falling within a designated range of clock pulses, according to:

$$M = \frac{\sum_{m=1}^{n_1} M_1(m) + \sum_{m=1}^{n_2} M_2(m)}{n_1 + n_2}$$

where M is the moisture content of the material expressed as a percentage by weight, wet-basis, $M_1(m)$ is the moisture content of the material determined using an mth selected first discharge duration, where m is an integer between 1 and $n_1$, inclusive, and $M_2(m)$ is the moisture content of the material determined using an mth selected second discharge duration, where m is an integer between 1 and $n_2$, inclusive.

6. The apparatus of claim 1 further comprising:

the first electrodes including parallel linear electrical conductors, each of the parallel linear electrical conductors being electrically insulated from each of the other parallel linear electrical conductors;

the second electrodes including parallel linear electrical conductors, each of the parallel linear electrical conductors being electrically insulated from each of the other parallel linear electrical conductors; and the ground electrodes including discrete parallel linear electrical conductors which are parallel to the first and second electrode parallel linear electrical conductors, each of the ground electrode discrete parallel linear electrical conductors being electrically insulated from each of the first and second electrode parallel linear electrical conductors, and each of the ground electrode discrete parallel linear electrical conductors being at an electrical ground potential.

7. The apparatus of claim 1 wherein the material is cotton in a cotton gin.

8. An apparatus for measuring moisture content of cotton based upon rates of electrical charges flowing through the cotton, the apparatus comprising:

a moisture sensor having:
 first electrodes having parallel linear electrical conductors, each of the parallel linear electrical conductors being electrically insulated from each of the other parallel linear electrical conductors;

second electrodes having parallel linear electrical conductors, each of the parallel linear electrical conductors being electrically insulated from each of the other parallel linear electrical conductors; and ground electrodes having discrete parallel linear electrical conductors which are interdigitated between and parallel to the first and second electrode parallel linear electrical conductors, each of the ground electrode discrete parallel linear electrical conductors being electrically insulated from the first and second electrode parallel linear electrical conductors, and each of the ground electrode discrete parallel linear electrical conductors being at an electrical ground potential; and a moisture content determination circuit having:

electrode charging circuits including:

first electrode charging circuits, each having a first capacitor with a capacitance of one microfarad associated with one of the first electrodes, the first capacitor charged to a first voltage level, the first voltage level applied to the associated one of the first electrodes; and second electrode charging circuits, each having a second capacitor with a capacitance of 270 picofarads associated with one of the second electrodes, the second capacitor charged to the first voltage level, the first voltage level applied to the associated one of the second electrodes;

a discharge timer for determining first discharge durations associated with the first electrodes and for determining second discharge durations associated with the second electrodes, the first discharge durations measuring the rates at which the first voltage level on the first electrodes decreases to a second voltage level as the first capacitors discharge, the second discharge durations measuring the rates at which the first voltage level on the second electrodes decreases to the second voltage level as the second capacitors discharge, the discharge timer having:

a clock for producing periodic clock pulses at a rate of two megahertz; and at least one counter for counting the clock pulses while the first voltage level on the first electrodes decreases to the second voltage level as the first capacitors discharge, and for counting the clock pulses while the first voltage level on the second electrodes decreases to the second voltage level as the second capacitors discharge; and a moisture content calculator for determining the moisture content of the cotton based only upon a number of selected first discharge durations and a number of selected second discharge durations, the selected first discharge durations and selected second discharge durations falling within a designated range of clock pulses, the moisture content calculator determining the moisture content of the cotton according to:

$$M = \frac{\sum_{m=1}^{n_1} M_1(m) + \sum_{m=1}^{n_2} M_2(m)}{n_1 + n_2},$$

where M is the moisture content of the cotton expressed as a percentage by weight, wet-basis, $$M_1(m) = \ln\left[\left(\frac{1.171 \times 10^{13}}{N_1(m)}\right)^{0.663}\right],$$

$$M_2(m) = \ln\left[\left(\frac{3.396 \times 10^9}{N_2(m)}\right)^{0.663}\right],$$

and where the designated range of clock pulses is between about 2000 clock pulses and about $10^7$ clock pulses, $n_1$ is the number of selected first discharge durations, $n_2$ is the number of selected second discharge durations, $M_1(m)$ is the moisture content of the cotton determined using an mth selected first discharge duration, where m is an integer between 1 and $n_1$, inclusive, $M_2(m)$ is the moisture content of the cotton determined using an mth selected second discharge duration, where m is an integer between 1 and $n_2$, inclusive, $N_1(m)$ is the mth selected first discharge duration in clock pulses, and $N_2(m)$ is the mth selected second discharge duration in clock pulses.

9. A method of measuring moisture content of a material based upon rates of electrical charges flowing through the material, the method comprising the steps of:

providing first electrical charges to first electrodes;

providing second electrical charges to second electrodes, where the first electrical charges and the second electrical charges are at different levels of charge;

discharging the first electrical charges through the material to ground electrodes interdigitated between the first and second electrodes;

discharging the second electrical charges through the material to the ground electrodes;

determining the rates of electrical charges flowing from the first electrodes through the material to the ground electrodes;

determining the rates of electrical charges flowing from the second electrodes through the material to the ground electrodes; and determining the moisture content of the material based upon the rates of electrical charges flowing from the first electrodes, and based upon the rates of electrical charges flowing from the second electrodes.

10. The method of claim 9 wherein:

the step of providing first electrical charges to the first electrodes includes the steps of:

charging first capacitors to a first voltage level; and applying the first voltage level to the first electrodes; and the step of providing second electrical charges to the second electrodes includes the steps of:

charging second capacitors to the first voltage level; and applying the first voltage level to the second electrodes.

11. The method of claim 10 wherein:

the step of determining the rates of electrical charges flowing from the first electrodes through the material to the ground electrodes includes the step of determining first discharge durations associated with the first electrodes, the first discharge durations measuring the rates at which the first voltage level on the first electrodes decreases to a second voltage level as the first capacitors discharge; and the step of determining the rates of electrical charges flowing from the second electrodes through the material to the ground electrodes includes the step of determining second discharge durations associated with the second electrodes, the second discharge durations measuring the rates at which the first voltage level on the second electrodes decreases to the second voltage level as the second capacitors discharge.

12. The method of claim 11 wherein:
the step of determining first discharge durations associated with the first electrodes includes the steps of:
producing periodic clock pulses; and
counting the clock pulses while the first voltage level on the first electrodes decreases to the second voltage level as the first capacitors discharge; and
the step of determining second discharge durations associated with the second electrodes includes the steps of:
producing periodic clock pulses; and
counting the clock pulses while the first voltage level on the second electrodes decreases to the second voltage level as the second capacitors discharge.

13. The method of claim 12 wherein the step of determining the moisture content of the material is based only upon a number of selected first discharge durations and a number of selected second discharge durations, the selected first discharge durations and selected second discharge durations falling within a designated range of clock pulses.

14. A method of measuring moisture content of a material based upon rates of electrical charges flowing through the material, the method comprising the steps of:
providing first electrical charges to first electrodes by charging first capacitors to a first voltage level, and applying the first voltage level to the first electrodes;
providing second electrical charges to second electrodes by charging second capacitors to the first voltage level, and applying the first voltage level to the second electrodes, where the first electrical charges and the second electrical charges are at different levels of charge;
discharging the first electrical charges through the material to ground electrodes interdigitated between the first and second electrodes;
discharging the second electrical charges through the material to the ground electrodes;
determining the rates of electrical charges flowing from the first electrodes through the material to the ground electrodes by determining first discharge durations associated with the first electrodes, the first discharge durations measuring the rates at which the first voltage level on the first electrodes decreases to a second voltage level as the first capacitors discharge, by producing periodic clock pulses and counting the periodic clock pulses while the first voltage level on the first electrodes decreases to the second voltage level as the first capacitors discharge;
determining the rates of electrical charges flowing from the second electrodes through the material to the ground electrodes by determining second discharge durations associated with the second electrodes, the second discharge durations measuring the rates at which the first voltage level on the second electrodes decreases to the second voltage level as the second capacitors discharge, by producing periodic clock pulses and counting the periodic clock pulses while the first voltage level on the second electrodes decreases to the second voltage level as the second capacitors discharge; and, determining the moisture content of the material based only upon a number of selected first discharge durations and a number of selected second discharge durations, the selected first discharge durations and selected second discharge durations falling within a designated range of clock pulses, according to:

$$M = \frac{\sum_{m=1}^{n_1} M_1(m) + \sum_{m=1}^{n_2} M_2(m)}{n_1 + n_2}$$

where M is the moisture content of the material expressed as a percentage by weight, wet-basis, $M_1(m)$ is the moisture content of the material determined using an mth selected first discharge duration, where m is an integer between 1 and $n_1$, inclusive, and $M_2(m)$ is the moisture content of the material determined using an mth selected second discharge duration, where m is an integer between 1 and $n_2$, inclusive.

15. The method of claim 9 wherein the material is cotton in a cotton gin.

16. A method of measuring moisture content of cotton based upon rates of electrical charges flowing through the cotton, the method comprising the steps of:
providing first electrical charges to first electrodes by:
charging first capacitors having a capacitance of one microfarad to a first voltage level; and
applying the first voltage level to the first electrodes;
providing second electrical charges to second electrodes by:
charging second capacitors having a capacitance of 270 picofarads to the first voltage level; and
applying the first voltage level to the second electrodes;
discharging the first electrical charges through the cotton to ground electrodes which are interdigitated between the first and second electrodes;
discharging the second electrical charges through the cotton to the ground electrodes;
determining first discharge durations associated with the first electrodes, the first discharge durations measuring the rates at which the first voltage level on the first electrodes decreases to a second voltage level as the first capacitors discharge, the step of determining the first discharge durations associated with the first electrodes including the steps of:
producing periodic clock pulses at a rate of two megahertz; and
counting the clock pulses while the first voltage level on the first electrodes decreases to the second voltage level as the first capacitors discharge;
determining second discharge durations associated with the second electrodes, the second discharge durations measuring the rates at which the first voltage level on the second electrodes decreases to the second voltage level as the second capacitors discharge, the step of determining the second discharge durations associated with the second electrodes including the steps of:
producing periodic clock pulses at a rate of two megahertz; and
counting the clock pulses while the first voltage level on the second electrodes decreases to the second voltage level as the second capacitors discharge; and determining the moisture content of the cotton based upon a number of selected first discharge durations and a number of selected second discharge durations, the selected first discharge durations and the selected second discharge durations falling within a designated range of clock pulses, the step of determining the moisture content of the cotton being performed according to:

$$M = \frac{\sum_{m=1}^{n_1} M_1(m) + \sum_{m=1}^{n_2} M_2(m)}{n_1 + n_2},$$

where M is the moisture content of the cotton expressed as a percentage by weight, wet-basis, $$M_1(m) = \ln\left[\left(\frac{1.171 \times 10^{13}}{N_1(m)}\right)^{0.663}\right],$$

$$M_2(m) = \ln\left[\left(\frac{3.396 \times 10^9}{N_2(m)}\right)^{0.663}\right],$$

and where the designated range of clock pulses is between about 2000 clock pulses and about $10^7$ clock pulses, $n_1$ is the number of selected first discharge durations, $n_2$ is the number of selected second discharge durations, $M_1(m)$ is the moisture content of the cotton determined using an mth selected first discharge duration, where m is an integer between 1 and $n_1$, inclusive, $M_2(m)$ is the moisture content of the cotton determined using an mth selected second discharge duration, where m is an integer between 1 and $n_2$, inclusive, $N_1(m)$ is the mth selected first discharge duration in clock pulses, and $N_2(m)$ is the mth selected second discharge duration in clock pulses.

17. An apparatus for measuring moisture content of a material based upon rates of electrical charges flowing through the material, the apparatus comprising:

a moisture sensor having:
sensor electrodes, and
ground electrodes interdigitated between the sensor electrodes; and a moisture content determination circuit for providing first electrical charges to the sensor electrodes and providing second electrical charges to the sensor electrodes, where the first electrical charges and the second electrical charges are at different levels of charge, for measuring the rates of the first electrical charges and the second electrical charges flowing from the sensor electrodes through the material to the ground electrodes, and for determining the moisture content of the material based upon the rates of the first and second electrical charges flowing through the material, the moisture content determination circuit including:
charging circuits including:
first charging circuits for providing the first electrical charges to the sensor electrodes each one of the first charging circuits applies a third voltage level to an associated one of the sensor electrodes, and
second charging circuits for providing the second electrical charges to the sensor electrodes each one of the second charging circuits applies a fourth voltage level to an associated one of the sensor electrodes;

a discharge timer for determining first discharge durations associated with the first electrical charges and for determining second discharge durations associated with the second electrical charges, the first discharge durations measuring the rates at which the first electrical charges on the sensor electrodes discharge through the material, the first discharge durations determined by measuring the rates at which the third voltage level decreases to a fifth voltage level as the first electrical charges on the sensor electrodes discharge through the material, the second discharge durations measuring the rates at which the second electrical charges on the sensor electrodes discharge through the material, the second discharge durations determined by measuring the rates at which the fourth voltage level decreases to a sixth voltage level as the second electrical charges on the sensor electrodes discharge through the material; and a moisture content calculator for determining the moisture content of the material based upon the first and second discharge durations.

18. A method of measuring moisture content of a material based upon first and second rates of electrical charges flowing through the material, the method comprising the steps of:

providing first electrical charges to the material by charging first capacitors to a first voltage level, and applying the first voltage level to sensor electrodes which contact the material;

providing second electrical charges to the material by charging second capacitors to the first voltage level, and applying the first voltage level to the sensor electrodes, where the second and first electrical charges are at different levels of charge;

discharging the first electrical charges through the material;

discharging the second electrical charges through the material;

determining the first rates of electrical charges flowing through the material as the first electrical charges discharge, by determining first discharge durations associated with the first electrical charges, the first discharge durations measuring the first rates at which the first voltage level on the sensor electrodes decreases to a second voltage level as the first capacitors discharge, by producing periodic clock pulses and counting the periodic clock pulses while the first voltage level on the sensor electrodes decreases to the second voltage level as the first capacitors discharge;

determining the second rates of electrical charges flowing through the material as the second electrical charges discharge, by determining second discharge durations associated with the second electrical charges, the second discharge durations measuring the second rates at which the first voltage level on the sensor electrodes decreases to the second voltage level as the second capacitors discharge, by producing periodic clock pulses and counting the clock pulses while the first voltage level on the sensor electrodes decreases to the second voltage level as the second capacitors discharge; and, determining the moisture content of the material based only upon a number of selected first discharge durations and a number of selected second discharge durations, the selected first discharge durations and selected second discharge durations falling within a designated range of clock pulses, according to:

$$M = \frac{\sum_{m=1}^{n_1} M_1(m) + \sum_{m=1}^{n_2} M_2(m)}{n_1 + n_2}$$

where M is the moisture content of the material expressed as a percentage by weight, wet-basis, $M_1(m)$ is the moisture content of the material determined using an mth selected first discharge duration, where m is an integer between 1 and $n_1$, inclusive, and $M_2(m)$ is the moisture content of the material determined using an mth selected second discharge duration, where m is an integer between 1 and $n_2$, inclusive.

19. A method of measuring moisture content of a material based upon first and second rates of electrical charges flowing through the material, the method comprising the steps of:

providing first electrical charges to the material by applying a third voltage level to sensor electrodes which contact the material;

providing second electrical charges to the material by applying a fourth voltage level to the sensor electrodes, where the second and first electrical charges are at different levels of charge;

discharging the first electrical charges through the material;

discharging the second electrical charges through the material;

determining the first rates of electrical charges flowing through the material as the first electrical charges discharge by determining first discharge durations associated with the first electrical charges, the first discharge durations measuring the first rates at which the third voltage level on the sensor electrodes decreases to a fifth voltage level as the first electrical charges on the sensor electrodes discharge through the material;

determining the second rates of electrical charges flowing through the material as the second electrical charges discharge by determining second discharge durations associated with the second electrical charges, the second discharge durations measuring the second rates at which the fourth voltage level on the sensor electrodes decreases to a sixth voltage level as the second electrical charges on the sensor electrodes discharge through the material; and determining the moisture content of the material based upon the first and second rates of electrical charges flowing through the material as the first and second electrical charges discharge.

20. The apparatus of claim 17 wherein:

each one of the first charging circuits has a first capacitor associated with one of the sensor electrodes, the first capacitor charged to a first voltage level which is applied to the associated one of the sensor electrodes;

each one of the second charging circuits has a second capacitor associated with one of the sensor electrodes, the second capacitor charged to the first voltage level which is applied to the associated one of the sensor electrodes; and the discharge timer determines the first discharge durations by measuring the rates at which the first voltage level on the sensor electrodes decreases to a second voltage level as the first capacitors discharge, and determines the second discharge durations by measuring the rates at which the first voltage level on the sensor electrodes decreases to the second voltage level as the second capacitors discharge.

21. The apparatus of claim 20 wherein the discharge timer further comprises:

a clock for producing periodic clock pulses; and at least one counter for counting the clock pulses while the first voltage level decreases to the second voltage level as the first capacitors discharge, and for counting the clock pulses while the first voltage level decreases to the second voltage level as the second capacitors discharge.

22. The apparatus of claim 21 wherein the moisture content calculator determines the moisture content of the material based only upon a number of selected first discharge durations and a number of selected second discharge durations, the selected first discharge durations and selected second discharge durations falling within a designated range of clock pulses.

23. An apparatus for measuring moisture content of a material based upon rates of electrical charges flowing through the material, the apparatus comprising:

a moisture sensor having:
sensor electrodes, and
ground electrodes interdigitated between the sensor electrodes; and a moisture content determination circuit for providing first electrical charges to the sensor electrodes and providing second electrical charges to the sensor electrodes, where the first electrical charges and the second electrical charges are at different levels of charge, for measuring the rates of the first electrical charges and the second electrical charges flowing from the sensor electrodes through the material to the ground electrodes, and for determining the moisture content of the material based upon the rates of the first and second electrical charges flowing through the material, the moisture content circuit including:

charging circuits including:
first charging circuits for providing the first electrical charges to the sensor electrodes, each one of the first charging circuits has a first capacitor associated with one of the sensor electrodes, the first capacitor charged to a first voltage level which is applied to the associated one of the sensor electrodes, and second charging circuits for providing the second electrical charges to the sensor electrodes, each one of the second charging circuits has a second capacitor associated with one of the sensor electrodes, the second capacitor charged to the first voltage level which is applied to the associated one of the sensor electrodes:

a discharge timer for determining first discharge durations associated with the first electrical charges and for determining second discharge durations associated with the second electrical charges, the first discharge durations measuring the rates at which the first electrical charges on the sensor electrodes discharge through the material, the second discharge durations measuring the rates at which the second electrical charges on the sensor electrodes discharge through the material, the discharge timer determining the first discharge durations by measuring the rates at which the first voltage level on the sensor electrodes decreases to a second voltage level as the first capacitors discharge, and determining the second discharge durations by measuring the rates at which the first voltage level on the sensor electrodes decreases to the second voltage level as the second capacitors discharge, the discharge timer including:
a clock for producing periodic clock pulses; and
at least one counter for counting the clock pulses while the first voltage level decreases to the second voltage level as the first capacitors discharge, and for counting the clock pulses while the first voltage level decreases to the second voltage level as the second capacitors discharge; and,
a moisture content calculator that determines the moisture content of the material based only upon a number of selected first discharge durations and a number of selected second discharge durations, the selected first discharge durations and selected second discharge durations falling within a designated range of clock pulses, according to:

$$M = \frac{\sum_{m=1}^{n_1} M_1(m) + \sum_{m=1}^{n_2} M_2(m)}{n_1 + n_2}$$

where M is the moisture content of the material expressed as a percentage by weight, wet-basis,
$M_1(m)$ is the moisture content of the material determined using an mth selected first discharge duration, where m is an integer between 1 and $n_1$, inclusive, and
$M_2(m)$ is the moisture content of the material determined using an mth selected second discharge duration, where m is an integer between 1 and $n_2$, inclusive.

24. The apparatus of claim 17 further comprising:
the sensor electrodes including parallel linear electrical conductors, each of the parallel linear electrical conductors being electrically insulated from each of the other parallel linear electrical conductors; and
the ground electrodes including discrete parallel linear electrical conductors which are parallel to the sensor electrode parallel linear electrical conductors, each of the ground electrode discrete parallel linear electrical conductors being electrically insulated from each of the sensor electrode parallel linear electrical conductors, and each of the ground electrode discrete parallel linear electrical conductors being at an electrical ground potential.

25. The apparatus of claim 17 wherein the material is cotton in a cotton gin.

26. The method of claim 19 wherein:
the step of providing first electrical charges to the material includes the steps of:
charging first capacitors to a first voltage level; and
applying the first voltage level to sensor electrodes which contact the material;
the step of providing second electrical charges to the material includes the steps of:
charging second capacitors to the first voltage level; and
applying the first voltage level to the sensor electrodes;
the step of determining the first rates of electrical charges flowing through the material includes the step of determining first discharge durations associated with the first electrical charges, the first discharge durations measuring the first rates at which the first voltage level on the sensor electrodes decreases to a second voltage level as the first capacitors discharge; and
the step of determining the second rates of electrical charges flowing through the material includes the step of determining second discharge durations associated with the second electrical charges, the second discharge durations measuring the second rates at which the first voltage level on the sensor electrodes decreases to the second voltage level as the second capacitors discharge.

27. The method of claim 26 wherein:
the step of determining first discharge durations associated with the first electrical charges includes the steps of:
producing periodic clock pulses; and
counting the clock pulses while the first voltage level on the sensor electrodes decreases to the second voltage level as the first capacitors discharge; and
the step of determining second discharge durations associated with the second electrical charges includes the steps of:
producing periodic clock pulses; and
counting the clock pulses while the first voltage level on the sensor electrodes decreases to the second voltage level as the second capacitors discharge.

28. The method of claim 27 wherein the step of determining the moisture content of the material is based only upon a number of selected first discharge durations and a number of selected second discharge durations, the selected first discharge durations and selected second discharge durations falling within a designated range of clock pulses.

29. The method of claim 19 wherein the material is cotton in a cotton gin.

* * * * *